United States Patent [19]
Baker et al.

[11] Patent Number: 5,278,049
[45] Date of Patent: Jan. 11, 1994

[54] RECOMBINANT MOLECULE ENCODING HUMAN PROTEASE NEXIN

[75] Inventors: Joffre B. Baker, Lawrence, Kans.; Randy W. Scott, San Carlos, Calif.

[73] Assignee: Incyte Pharmaceuticals, Inc., Redwood City, Calif.

[21] Appl. No.: 25,450

[22] Filed: Mar. 13, 1987

Related U.S. Application Data

[63] Continuation-in-part of Ser. No. 871,501, Jun. 6, 1986, abandoned, which is a continuation-in-part of Ser. No. 870,232, Jun. 3, 1986, abandoned.

[51] Int. Cl.$^5$ .................. C12P 21/00; C12P 19/34; C12N 15/00; C12N 9/48; C12N 9/50; C12N 7/00; C12N 5/00; C12N 1/21; C12N 1/16; C12N 1/18; C07H 15/12; C07K 3/00
[52] U.S. Cl. .................. 435/68.1; 435/91.4; 435/172.3; 435/212; 435/219; 435/235.1; 435/320.1; 435/252.3; 435/240.2; 435/254.21; 536/23.5; 536/24.31; 530/350; 935/18; 935/32; 935/41; 935/57; 935/61; 935/70; 935/82
[58] Field of Search ............. 435/68, 70, 172.3, 212, 435/219, 69.1, 71.1, 91, 252.33, 235.1, 320.1, 240.2, 255, 256; 536/27; 530/350

[56] References Cited

FOREIGN PATENT DOCUMENTS 0233838 8/1987 European Pat. Off. .

OTHER PUBLICATIONS

Scott, R. W. et al. J. Biol. Chem. vol. 258 pp. 10439-10444 (1983).
Scott, R. W. et al J. Biol. Chem. vol. 260 pp. 7029-7034 (1985).
Suggs, S. V. et al Proc. Natl. Acad. Sci. USA vol. 78 pp. 6613-6617 (1981).
Maniatis, T. et al. Molecular Cloning, A Laboratory Manual Cold Spring Harbor Laboratory C&H, N.Y. (1982).
British Priority Document Case Ref. 4-15735-/1-3/ZFM/B.862 Jul. 31, 1986.
British Priority document Case Ref. 4-15735/1+2/ZFM/B.862 Feb. 11, 1986.
British Priority Document Case Ref. 4-15735/ZFM/B.862 Feb. 4, 1986.
Proteases in Biological Control (1975) Reich et al., eds. Cold Spring Harbor, New York, pp. 1-10.
Jones et al., (1980) Cancer Research 40:3222-3227.
Bergman et al., (1986) Proc. Natl. Acad. Sci. USA 83:996-1000.
McGuire-Goldring et al., (1984) Arth. Rheum. 27:S24.
Monrad et al., (1983) Prog Brain Res 58:359-364.
Erickson, L. A., Proc Natl Acad Sci, 82: 8710-8714, (1985), "The primary plasminogen-activator inhibitors in endothelial cells, platelets, serum, and plasma are immunologically related".
Ny, T. et al, Proc Natl Acad Sci, 83:6776-6780, (1986), "Cloning and sequence of a cDNA coding for the human beta-migrating endothelial-cell-type plasminogen activator inhibitor".
Scott, R. W., Chemical Abstracts, 103, No. 3, (1985), "Protease Nexin. Properties and modified purification procedure".
Eaton, D. L., Chemical Abstracts, 101, No. 7, (1984), "Purification of human fibroblast urokinase proenzyme and analysis of its regulation by proteases and protease nexin".
Gloor, S., Biological Abstracts, 83, No. 7, (1987), "A glia-derived neurite promoting factor with protease inhibitory activity belongs to the protease nexins".

Primary Examiner—Joan Ellis
Attorney, Agent, or Firm—Karl Bozicevic; Kate H. Murashige

[57] ABSTRACT

DNA segments encoding two slightly different protease nexin I forms (PN-Iα and PN-Iβ) are cloned and expressed to provide practical quantities of PN-I for diagnostic and therapeutic use. PN-I is a serine protease inhibitor useful in controlling conditions mediated by proteolytic activity.

9 Claims, 10 Drawing Sheets

FIG. 1a

```
                        20              24
AMINO ACID      Phe Asn Gln Ile Val
CODON       5'  TTT AAT CAA ATT GT    3'
                 C   C   G   C
                             A
```

REVERSE COMPLEMENT 14MER:

```
        5'  ACAATTTGATTAAA  3'
              G   C   G G
              T
```

FIG. 1b

AMINO ACID SEQUENCE:

```
     14                  20                  25
  Asn Thr Gly Ile Gln Val Phe Asn Gln Ile Val Lys
```

CONSENSUS 36MER:

```
     1           12          24          36
5' AAC ACC GGC ATC CAG GTG TTC AAT CAG ATC GTG AAG  3'
    T   T                               T   C
```

SEQUENCE OF PROTEASE NEXIN I TYPE ALPHA

CTGTGACCCTCCTCGCCGCCGCCGCTTCGCTCGCTCCTCCGACTCCCCGCCGCCGAGACTAGG

CTCCGCTCCGGTTGCGGCGACCCCTCCGCGGCCGCCCCTGGGGATCCAGCGAGCG

```
                                 S1
CGGTCGTCCTTGGTGGAAGGAACC     ATG AAC TGG CAT CTC CCC CTC TTC CTC
                             Met Asn Trp His Leu Pro Leu Phe Leu

S10                                            1
TTG GCC TCT GTG ACG CTG CCT TCC ATC TGC TCC CAC TTC AAT
Leu Ala Ser Val Thr Leu Pro Ser Ile Cys Ser His Phe Asn 10                                        20
CCT CTG TCT CTC GAG GAA CTA GGC TCC AAC ACG GGG ATC CAG GTT TTC
Pro Leu Ser Leu Glu Glu Leu Gly Ser Asn Thr Gly Ile Gln Val Phe

30
AAT CAG ATT GTG AAG TCG AGG CCT CAT GAC AAC ATC GTG ATC
Asn Gln Ile Val Lys Ser Arg Pro His Asp Asn Ile Val Ile 40                                   50
TCT CCC CAT GGG ATT GCG TCG GTC CTG GGG ATG CTT CAG CTG GGG GCG
Ser Pro His Gly Ile Ala Ser Val Leu Gly Met Leu Gln Leu Gly Ala

60
GAC GGC AGG ACC AAG AAG CAG CTC GCC ATG GTG ATG AGA TAC
Asp Gly Arg Thr Lys Lys Gln Leu Ala Met Val Met ARg Tyr 70                                   80
GGC GTA AAT GGA GTT GGT AAA ATA TTA AAG AAG ATC AAC AAG GCC ATC
Gly VAl Asn Gly Val Gly Lys Ile Leu Lys Lys Ile Asn Lys Ala Ile

90
GTC TCC AAG AAG AAT AAA GAC ATT GTG ACA GTG GCT AAC GCC
Val Ser Lys Lys Asn Lys Asp Ile Val Thr Val Ala Asn Ala 100                                  110
GTG TTT GTT AAG AAT GCC TCT GAA ATT GAA GTG CCT TTT GTT ACA AGG
Val Phe Val Lys Asn Ala Ser Glu Ile Glu Val Pro Phe Val Thr Arg

120
AAC AAA GAT GTG TTC CAG TGT GAG GTC CGG AAT GTG AAC TTT
Asn Lys Asp Val Phe Gln Cys Glu Val Arg Asn Val Asn Phe 130                                  140
GAG GAT CCA GCC TCT GCC TGT GAT TCC ATC AAT GCA TGG GTT AAA AAT
Glu Asp Pro Ala Ser Ala Cys Asp Ser Ile Asn Ala Trp Val Lys Asn

150           BglII
GAA ACC AGG GAT ATG ATT GAC AAT CTG CTG TCC CCA GAT CTT
Glu Thr Arg Asp Met Ile Asp Asn Leu Leu Ser Pro Asp Leu
```

FIG.3-1

```
                              160                                              170
ATT GAT GGT GTG CTC ACC AGA CTG GTC CTC GTC AAC GCA GTG TAT TTC
Ile Asp Gly Val Leu Thr Arg Leu Val Leu Val Asn Ala Val Tyr Phe

180
AAG GGT CTG TGG AAA TCA CGG TTC CAA CCC GAG AAC ACA AAG
Lys Gly Leu Trp Lys Ser Arg Phe Gln Pro Glu Asn Thr Lys 190                                              200
AAA CGC ACT TTC GTG GCA GCC GAC GGG AAA TCC TAT CAA GTG CCA ATG
Lys Arg Thr Phe Val Ala Ala Asp Gly Lys Ser Tyr Gln Val Pro Met

210 SalI
CTG GCC CAG CTC TCC GTG TTC CGG TGT GGG TCG ACA AGT GCC
Leu Ala Gln Leu Ser Val Phe Arg Cys Gly Ser Thr Ser Ala 220                                              230
CCC AAT GAT TTA TGG TAC AAC TTC ATT GAA CTG CCC TAC CAC GGG GAA
Pro Asn Asp Leu Trp Tyr Asn Phe Ile Glu Leu Pro Tyr His Gly Glu

240         SacI
AGC ATC AGC ATG CTG ATT GCA CTG CCG ACT GAG AGC TCC ACT
Ser Ile Ser Met Leu Ile Ala Leu Pro Thr Glu Ser Ser Thr 250                                              260
CCG CTG TCT GCC ATC ATC CCA CAC ATC AGC ACC AAG ACC ATA GAC AGC
Pro Leu Ser Ala Ile Ile Pro His Ile Ser Thr Lys Thr Ile Asp Ser

270
TGG ATG AGC ATC ATG GTG CCC AAG AGG GTG CAG GTG ATC CTG
Trp Met Ser Ile Met Val Pro Lys Arg Val Gln Val Ile Leu 280                                              290
CCC AAG TTC ACA GCT GTA GCA CAA ACA GAT TTG AAG GAG CCG CTG AAA
Pro Lys Phe Thr Ala Val Ala Gln Thr Asp Leu Lys Glu Pro Leu Lys

300
GTT CTT GGC ATT ACT GAC ATG TTT GAT TCA TCA AAG GCA AAT
Val Leu Gly Ile Thr Asp Met Phe Asp Ser Ser Lys Ala Asn 310                                              320
TTT GCA AAA ATA ACA AGG TCA GAA AAC CTC CAT GTT TCT CAT ATC TTG
Phe Ala Lys Ile Thr Arg Ser Glu Asn Leu His Val Ser His Ile Leu

330         HindIII
CAA AAA GCA AAA ATT GAA GTC AGT GAA GAT GGA ACC AAA GCT
Gln Lys Ala Lys Ile Glu Val Ser Glu Asp Gly Thr Lys Ala 340                                              350
TCA GCA GCA ACA ACT GCA ATT CTC ATT GCA AGA TCA TCG CCT CCC TGG
Ser Ala Ala Thr Thr Ala Ile Leu Ile Ala Arg Ser Ser Pro Pro Trp 360
TTT ATA GTA GAC AGA CCT TTT CTG TTT TTC ATC CGA CAT AAT
Phe Ile Val Asp Arg Pro Phe Leu Phe Phe Ile Arg His Asn
```

FIG.3-2

```
                       370                                          378
CCT ACA GGT GCT GTG TTA TTC ATG GGG CAG ATA AAC AAA CCC TGA AGAGT
Pro Thr Gly Ala Val Leu Phe Met Gly Gln Ile Asn Lys Pro ---
```

ATACAAAAGAAACCATGCAAAGCAACGACTACTTTGCTACGAAGAAAGACTCCT

TTCCTGCATCTTTCTGTTAAATATTCTTGTACATCGCATTCTTTTTCAAAACGTAGTTTCTTAGG

AAGCAGACTCGATGCAACTGTTCCTGTTCTGGGAGGTATTGGAGGGAAAAAACA

AGCAGGATGCCTGGCACAGCTGTACTGAGGATTGATATAGAAAGACTTCCAGATGCCTAAAAGAT

TCTTTAAACTACTGAACTGTTACCTAGGTTAACATCCCTGTTGAGGTATTTGCT

GTTTGTCCAGTTAGGAATTTTTGTTTTGTTTTGCTCTATATGTGCGGCTTTTCAGAAGAAATTTA

ATCAGTGTGACAGAAAAAAAAAATGTTTTATGGTAGCTTTTACTTTTTATGAAA

AAAAAATTATTTGTTCCTTTTAAATTCTTTTCCCCCATCCCCCTCCAAAGTCTTGATAGCAAGCG

TTATTTTGGGGGTAGAAACGGTGAAATCTCTAGCCTCTTTGTGTTTTTGTTGTT

GTTGTTGTTGTTGTTTTATATAATGCATGTATTCACTAAAATAAAATTTAAAAAACGTCCTGTCT

TGCTAGACAAGGTTGTGCATGTGCCTGTCACTACTGAGTCTGTCTACCTATGGA

TTTGCATTTTTGTATTTTGTACAAAGTAAAAATAACT

FIG.3-3

SEQUENCE OF PROTEASE NEXIN I TYPE BETA

CTGTGACCCTCCTCGCCGCCGCCGCTTCGCTCGCTCCTCCGACTCCCCCGCCGCCGAGACTAGG

CTCCGCTCCGGTTGCGGCGACCCCTCCGCGGCCGCCCCTGGGGATCCAGCGAGCG

```
                                       S1
CGGTCGTCCTTGGTGGAAGGAACC              ATG AAC TGG CAT CTC CCC CTC TTC CTC
                                      Met Asn Trp His Leu Pro Leu Phe Leu

S10                                                    1
TTG GCC TCT GTG ACG CTG CCT TCC ATC TGC TCC CAC TTC AAT
Leu Ala Ser Val Thr Leu Pro Ser Ile Cys Ser His Phe Asn 10                                              20
CCT CTG TCT CTC GAG GAA CTA GGC TCC AAC ACG GGG ATC CAG GTT TTC
Pro Leu Ser Leu Glu Glu Leu Gly Ser Asn Thr Gly Ile Gln Val Phe

30
AAT CAG ATT GTG AAG TCG AGG CCT CAT GAC AAC ATC GTG ATC
Asn Gln Ile Val Lys Ser Arg Pro His Asp Asn Ile Val Ile 40                                         50
TCT CCC CAT GGG ATT GCG TCG GTC CTG GGG ATG CTT CAG CTG GGG GCG
Ser Pro His Gly Ile Ala Ser Val Leu Gly Met Leu Gln Leu Gly Ala

60
GAC GGC AGG ACC AAG AAG CAG CTC GCC ATG GTG ATG AGA TAC
Asp Gly Arg Thr Lys Lys Gln Leu Ala Met Val Met ARg Tyr 70                                         80
GGC GTA AAT GGA GTT GGT AAA ATA TTA AAG AAG ATC AAC AAG GCC ATC
Gly VAl Asn Gly Val Gly Lys Ile Leu Lys Lys Ile Asn Lys Ala Ile

90
GTC TCC AAG AAG AAT AAA GAC ATT GTG ACA GTG GCT AAC GCC
Val Ser Lys Lys Asn Lys Asp Ile Val Thr Val Ala Asn Ala 100                                            110
GTG TTT GTT AAG AAT GCC TCT GAA ATT GAA GTG CCT TTT GTT ACA AGG
Val Phe Val Lys Asn Ala Ser Glu Ile Glu Val Pro Phe Val Thr Arg

120
AAC AAA GAT GTG TTC CAG TGT GAG GTC CGG AAT GTG AAC TTT
Asn Lys Asp Val Phe Gln Cys Glu Val Arg Asn Val Asn Phe 130                                        140
GAG GAT CCA GCC TCT GCC TGT GAT TCC ATC AAT GCA TGG GTT AAA AAT
Glu Asp Pro Ala Ser Ala Cys Asp Ser Ile Asn Ala Trp Val Lys Asn

150               BglII
GAA ACC AGG GAT ATG ATT GAC AAT CTG CTG TCC CCA GAT CTT
Glu Thr Arg Asp Met Ile Asp Asn Leu Leu Ser Pro Asp Leu
```

FIG.4-1

```
                                    160                                         170
ATT GAT GGT GTG CTC ACC AGA CTG GTC CTC GTC AAC GCA GTG TAT TTC
Ile Asp Gly Val Leu Thr Arg Leu Val Leu Val Asn Ala Val Tyr Phe

180
AAG GGT CTG TGG AAA TCA CGG TTC CAA CCC GAG AAC ACA AAG
Lys Gly Leu Trp Lys Ser Arg Phe Gln Pro Glu Asn Thr Lys 190                                         200
AAA CGC ACT TTC GTG GCA GCC GAC GGG AAA TCC TAT CAA GTG CCA ATG
Lys Arg Thr Phe Val Ala Ala Asp Gly Lys Ser Tyr Gln Val Pro Met

210 SalI
CTG GCC CAG CTC TCC GTG TTC CGG TGT GGG TCG ACA AGT GCC
Leu Ala Gln Leu Ser Val Phe Arg Cys Gly Ser Thr Ser Ala 220                                         230
CCC AAT GAT TTA TGG TAC AAC TTC ATT GAA CTG CCC TAC CAC GGG GAA
Pro Asn Asp Leu Trp Tyr Asn Phe Ile Glu Leu Pro Tyr His Gly Glu

240        SacI
AGC ATC AGC ATG CTG ATT GCA CTG CCG ACT GAG AGC TCC ACT
Ser Ile Ser Met Leu Ile Ala Leu Pro Thr Glu Ser Ser Thr 250                                             260
CCG CTG TCT GCC ATC ATC CCA CAC ATC AGC ACC AAG ACC ATA GAC AGC
Pro Leu Ser Ala Ile Ile Pro His Ile Ser Thr Lys Thr Ile Asp Ser

270
TGG ATG AGC ATC ATG GTG CCC AAG AGG GTG CAG GTG ATC CTG
Trp Met Ser Ile Met Val Pro Lys Arg Val Gln Val Ile Leu 280                                         290
CCC AAG TTC ACA GCT GTA GCA CAA ACA GAT TTG AAG GAG CCG CTG AAA
Pro Lys Phe Thr Ala Val Ala Gln Thr Asp Leu Lys Glu Pro Leu Lys

300
GTT CTT GGC ATT ACT GAC ATG TTT GAT TCA TCA AAG GCA AAT
Val Leu Gly Ile Thr Asp Met Phe Asp Ser Ser Lys Ala Asn 310                                         320
TTT GCA AAA ATA ACA ACA GGG TCA GAA AAC CTC CAT GTT TCT CAT ATC
Phe Ala Lys Ile Thr Thr Gly Ser Glu Asn Leu His Val Ser His Ile

330        HindIII
TTG CAA AAA GCA AAA ATT GAA GTC AGT GAA GAT GGA ACC AAA
Leu Gln Lys Ala Lys Ile Glu Val Ser Glu Asp Gly Thr Lys 340                                             350
GCT TCA GCA GCA ACA ACT GCA ATT CTC ATT GCA AGA TCA TCG CCT CCC
Ala Ser Ala Ala Thr Thr Ala Ile Leu Ile Ala Arg Ser Ser Pro Pro 360
TGG TTT ATA GTA GAC AGA CCT TTT CTG TTT TTC ATC CGA CAT
Trp Phe Ile Val Asp Arg Pro Phe Leu Phe Phe Ile Arg His
```

FIG.4-2

```
                                    370                              378
AAT CCT ACA GGT GCT GTG TTA TTC ATG GGG CAG ATA AAC AAA CCC TGA
Asn Pro Thr Gly Ala Val Leu Phe Met Gly Gln Ile Asn Lys Pro ---
```

AGAGTATACAAAAGAAACCATGCAAAGCAACGACTACTTTGCTACGAAGAAAGACT

CCTTTCCTGCATCTTTCTGTTAAATATTCTTGTACATCGCATTCTTTTTCAAAACGTAGTTTCT

TAGGAAGCAGACTCGATGCAACTGTTCCTGTTCTGGGAGGTATTGGAGGGAAAAA

ACAAGCAGGATGCCTGGCACAGCTGTACTGAGGATTGATATAGAAAGACTTCCAGATGCCTAAA

AGATTCTTTAAACTACTGAACTGTTACCTAGGTTAACATCCCTGTTGAGGTATTT

GCTGTTTGTCCAGTTAGGAATTTTTGTTTTGTTTTGCTCTATATGTGCGGCTTTTCAGAAGAAA

TTTAATCAGTGTGACAGAAAAAAAAAATGTTTTATGGTAGCTTTTACTTTTTATG

AAAAAAAAATTATTTGTTCCTTTTAAATTCTTTTCCCCCATCCCCCTCCAAAGTCTTGATAGCA

AGCGTTATTTTGGGGGTAGAAACGGTGAAATCTCTAGCCTCTTTGTGTTTTTGTT

GTTGTTGTTGTTGTTTTATATAATGCATGTATTCACTAAAATAAAATTTAAAAAACGTCCT

GTCTTGCTAGACAAGGTTGTGCATGTGCCTGTCACTACTGAGTCTGTCTACCTAT

GGATTTGCATTTTTGTATTTTGTACAAAGTAAAAATAACT

FIG.4-3

RECOMBINANT MOLECULE ENCODING HUMAN PROTEASE NEXIN

CROSS-REFERENCE TO RELATED APPLICATION

This is a continuation-in-part of U.S. Ser. No. 871,501, filed Jun. 6, 1986, which is a continuation-in-part of U.S. Ser. No. 870,232, filed Jun. 3, 1986.

TECHNICAL FIELD

The invention relates to recombinant production of proteins affecting the cardiovascular system. In particular, it concerns the cloning and expression of genes encoding forms of protease nexin I (PN-I).

BACKGROUND ART

Connective tissue cells secrete protease inhibitors which are specific for serine proteases. Since serine proteases are involved in development and migration of cells, regulation of the activity of these enzymes is necessary to exercise control over the remodeling or destruction of tissues (*Proteases in Biological Control* (1975), Reich, E., et al, eds., Cold Spring Harbor, New York). The inhibitors designated protease nexins irreversibly bind to serine proteases at their catalytic sites (Baker, J. B., et al, *Cell* (1980) 21:37–45) and effect the clearance of the bound proteases via receptor-mediated endocytosis and lysosomal degradation (Low, D. A., et al, *Proc Natl Acad Sci* (USA) (1981) 78:2340–2344; Baker, J. B., et al, in *The Receptors* 3 (1985), Conn. P. M., ed, Academic Press, in press).

Three protease nexins have been identified. Protease nexin I (PN-I) has been purified from serum-free medium conditioned by human foreskin cells (Scott, R. W., et al, *J Biol Chem* (1983) 58:10439–10444). It is a 43 kd glycoprotein which is released by fibroblasts, myotubes, heart muscle cells, and vascular smooth muscle cells. Its release, along with that of plasminogen activator, is stimulated by phorbol esters and by mitogens (Eaton, D. L., et al, *J Cell Biol* (1983) 123:128). Native PN-I is an approximately 400 amino acid protein containing about 6% carbohydrate. Since it is present only in trace levels in serum, it apparently functions at or near the surfaces of interstitial cells. PN-I inhibits all the known activators of urokinase proenzyme, plasmin, trypsin, thrombin, and factor Xa (Eaton, D. L., et al, *J Biol Chem* (1984) 259:6241). It also inhibits tissue plasminogen activator and urokinase.

A protein called neurite-promoting factor (NPF) has also been reported to be isolated from glioma cells, to have a 43 kd molecular weight, and to inhibit proteolysis catalyzed by urokinase or plasminogen activator (Guenther, J., et al. *EMBO Journal* (1985) 4:1963–1966). It was first reported as inducing neurite outgrowth in neuroblastoma cells (Barde, Y. A., et al, *Nature* (1978) 274:818). The amino acid sequence of this protein, but not the sequence of the cDNA encoding it, is disclosed in Gloor, S., et al, *Cell* (1986) 47:687–693. Any relationship between this DNA and those reported herein is uncertain, since the restriction map for the glial cDNA clearly differs from that of the cDNAs disclosed herein. The NPF protein is a 379 amino acid sequence preceded by an 18 amino acid, met-preceded signal. It differs from the PN-Iβ disclosed herein at amino acid posiiton 241 of the mature protein.

The need for practical amounts of purified PN-I is severalfold. First, PN-I has clear utility as a pharmaceutical for conditions characterized by excess amounts of urokinase and tissue plasminogen activator, or as an antidote for overdoses of these enzymes as agents for solution of blood clots. Indications which are clearly susceptible to PN-I treatment include the autoimmune disease penphigus, which is commonly encountered in dogs, and psoriasis, which is believed to be due to an overproduction of plasminogen activator. Second, because the role of PN-I in regulating various developmental stages of tissue formation and remodeling is relatively complex, it would be desirable to be able to use model systems to discern in greater detail the role PN-I plays. This can be done effectively only if practical quantities are available. Finally, PN-I is useful as an assay reagent in immunological assays for its levels in serum or in other tissues or for other biological assays.

Exemplary of the conditions for which further study of the role of PN-I is desirable are tumor metastasis, wound healing, and inflammation. In tumor metastasis, malignant cells must penetrate the extracellular matrix laid down by vascular smooth muscle cells, a process which is mediated by secreted plasminogen activator. In the model system of Jones, P. A., et al, *Cancer Res* (1980) 40:3222, an in vitro system based on the invasion of the extracellular matrix by human fibrosarcoma cells, it could be shown that PN-I at 0.1 μM causes virtually complete suppression of the invasion (Bergman, B. L., et al, *Proc Natl Acad Sci* USA (1986) 83:996–1000). The proteolytic activity of thrombin, which is a fibroblast mitogen important in wound healing, is effective only when added to cultures at concentrations above the concentrations of secreted PN-I (Baker, J. B., et al, *J Cell Physiol* (1982) 112:291; Low, D. A., et al, *Nature* (1982) 298: 2476). It has been suggested that PN-I has an anti-inflammatory function, since PN-I secretion by synovial fibroblasts increases dramatically when the cells are treated with interleukin-I (Krane, S., *Arth Rheum* (1984) 27:S24). PN-I may also have a neurological function, since the above-mentioned similar protease inhibitor stimulates neurite extension (Monard et al, *Prog Brain Res* (1983) 58:359).

Elucidation of the precise function of PN-I in any of the foregoing would be greatly simplified by the availability of the needed amounts of pure material. These amounts are also needed for use in PN-I as a pharmaceutical and in diagnosis and assay. The present invention provides a solution to the problem of obtaining sufficient quantities of PN-I, as well as a mechanism for modifying PN-I structure in order to make it more effective.

DISCLOSURE OF THE INVENTION

The invention provides a highly purified PN-I protein, including recombinant forms, and the DNA coding sequences, expression systems, and methods which permit the production of recombinant mammalian PN-I. Two exemplary forms of PN-I are disclosed.

By employing these materials and methods, desired quantities of the PN-I protein can be produced, either in glycosylated or unglycosylated form, depending on the expression systems employed, and the gene can be modified, if desired, to alter the precise amino acid sequence so as to enhance the desired properties of the protein. This is all possible through the availability of genes encoding human PN-I, which are directly useful in producing the corresponding PN-I, and are also useful as probes to retrieve cDNA sequences encoding these genes in a variety of species.

The human genes encoding two closely related PN-I proteins are illustrated below. Retrieval of PN-I encoding DNA of other species is also desirable; that encoding the murine protein(s) is particularly desirable, as many model systems for providing a detailed description of the role of such factors are conveniently based on murine cells, tissues, or whole organisms.

Thus, in one aspect the invention relates to DNA sequences encoding mammalian PN-I and to derivatives thereof, which can be expressed to obtain proteins with PN-I activity. In other aspects, the invention relates to cells transformed with these DNA sequences, and to the PN-I proteins produced by these cells. In addition, the invention relates to purified protein having the N-terminal sequence of the native protein as disclosed herein, to antibodies prepared by administration of the recombinant or purified native protein, and to DNA probes capable of retrieving PN-I cDNA.

BRIEF DESCRIPTION OF THE DRAWINGS

FIG. 1a shows the sequence of protease nexin oligomer probes which were employed to identify PN-I clones. The codons defined by amino acid residues 20-24 of protease nexin are shown under the amino acid sequence. The 14 mer mixed oligomer that was designed as the reverse complement of this coding sequence consists of a mixture of the 24 permutations.

FIG. 1b shows the sequences of protease nexin oligomer probes used to identify PN-I clones. A Consensus 36 mer is shown. Amino acid residues 14-25 of a protease nexin correspond to the least ambiguous coding sequence that define a 36-base oligomer. The Consensus 36 mer with four mixed sites at positions 3, 6, 30 and 33 was designed by using preferred codons to assign the remaining ambiguous bases as shown.

FIGS. 3-1 to 3-3 show the nucleotide sequence of the coding region of PN-18 and the deduced amino acid sequence of PN-Iα.

FIGS. 4-1 to 4-3 show the nucleotide sequence of the coding region of PN-33 and the deduced amino acid sequence of PN-Iβ.

Lane 1) 1 ug human fibroblast non-polyA RNA.
Lane 2) 6 ug human fibroblast polyA-RNA 1-23.
Lane 3) 8 ug human fibroblast polyA-RNA 1-6.
Lane 4) 8 ug human 293 cells polyA-RNA.
Lane 5) 8 ug BOWES melanoma polyA-RNA.
Lane 6) 5 ug SK HEPATOMA non-polyA RNA.

Figures 6, 7:
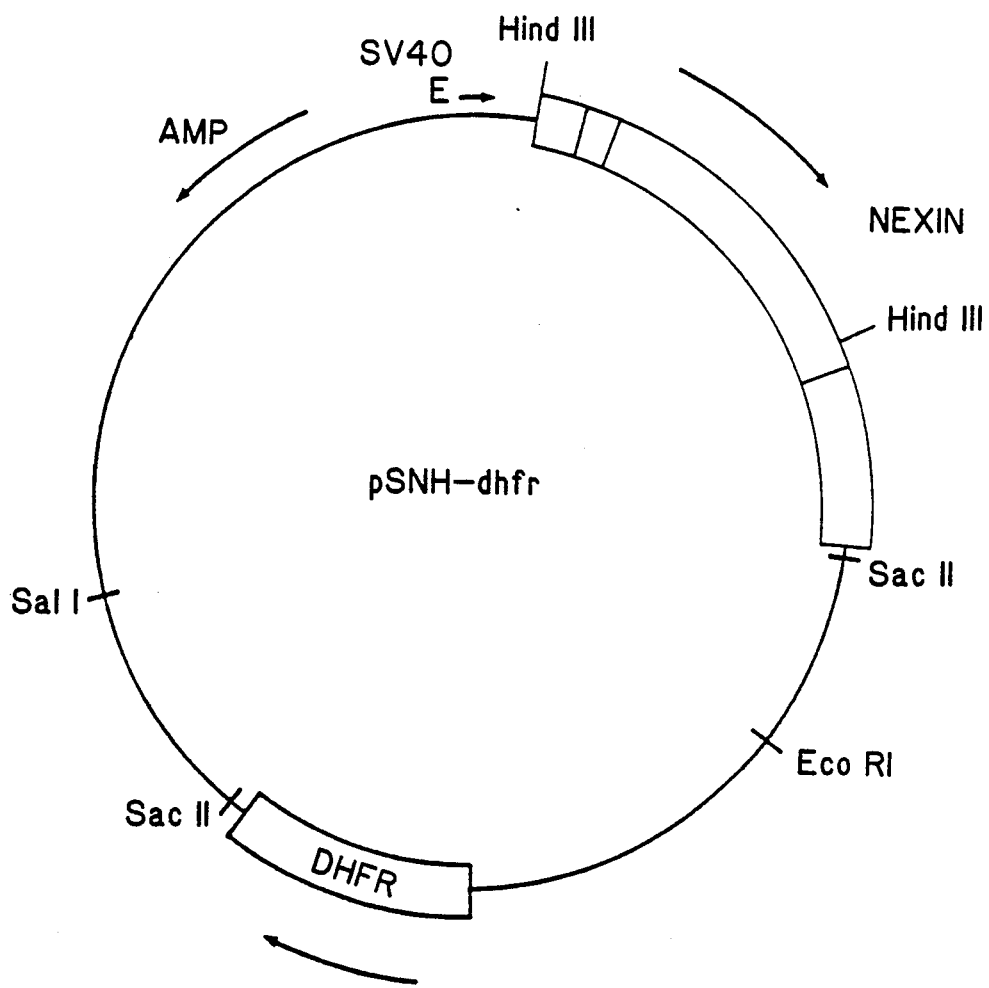

FIG. 6 shows the splice junction region of the PN-I gene which accounts for the production of the PN-Iα and PN-Iβ forms.

FIG. 7 shows the expression vector pFNH-dhfr.

MODES OF CARRYING OUT THE INVENTION

Definitions

As used herein, "protease nexin I" (PN-I) refers to a protein which is active in the standard diagnostic assays for PN-I, which are based on four criteria, as follows: (1) The protein complexes to thrombin; (2) this complexation is accelerated by heparin; (3) the protein binds to the cell of its origin, for example, in the illustration below, to fibroblasts; and (4) heparin must inhibit this binding.

PN-I is distinguishable from the two other protease nexin factors, PN-II and PN-III (Knauer, D. J., et al, *J Biol Chem* (1982) 257:15098-15104), which are also major thrombin inhibitors, but are less strongly binding to this protease.

"Control sequence" refers to a DNA sequence of sequences which are capable, when properly ligated to a desired coding sequence, of effecting its expression in hosts compatible with such sequences. Such control sequences include at least promoters in both procaryotic and eucaryotic hosts, and preferably, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant PN-I.

"Purified" or "pure" refers to material which is free from substances which normally accompany it as found in its native state. Thus "pure" PN-I-encoding DNA refers to DNA which is found in isolation from its native environment and free of association with DNAs encoding other proteins normally produced by cells natively producing PN-I. "Pure" PN-I refers to PN-I which does not contain materials normally associated with its in situ environment in human or other mammalian tissue. Of course, "pure" PN-I may include materials in covalent association with it, such as glycoside residues or materials introduced for, for example, formulation as a therapeutic. "Pure" simply designates a situation wherein the substance referred to is, or has been isolated from its native environment and materials which normally accompany it.

Of course, the DNA claimed herein as purified and free of substances normally accompanying it, but encoding PN-I, can include additional sequence at the 5' and/or 3' end of the coding sequence which might result, for example, from reverse transcription of the noncoding portions of the message when the DNA is derived from a cDNA library or might include the reverse transcript for the signal sequence as well as the mature protein encoding sequence.

"Degenerate with", as referred to a DNA sequence, refers to nucleotide sequences encoding the same amino acid sequence as that referenced.

"Operably linked" refers to a juxtaposition wherein the components are configured so as to perform their usual function. Thus, control sequences or promoters operably linked to a coding sequence are capable of effecting the expression of the coding sequence.

B. General Description

PN-I was purified to homogeneity from serum-free medium conditioned by human foreskin fibroblasts in microcarrier cultures by affinity chromatography on heparin-agarose, followed by gel-exclusion chromatography, as described in detail by Scott, R. W., et al, *J Biol Chem* (1985) 260:7029–7034, incorporated herein by reference. Of course, other chromatographic supports which contain heparin for affinity binding can also be used. The purified protein shows an $M_r$ of 42-43 kd, based on sedimentation equilibrium analysis, or of 47 kd, estimated from gel-exclusion chromatography. The purified material shows the properties exhibited by PN-I when contained in conditioned medium, including formation of sodium dodecylsulfate-stable complexes with thrombin, urokinase, and plasmin; inhibition of protease activity; heparin-enhanced inhibition of thrombin; and cellular binding of protease-PN complexes in a heparin-sensitive reaction. The purified native protein contains approximately 6% carbohydrate with 2.3% amino sugar, 1.1% neutral sugar, and 3.0% sialic acid. The N-terminal amino acid sequence of the isolated, purified protease nexin was determined for the first 34 amino acids to be: Ser-His-Phe-Asn-Pro-Leu-Ser-Leu-Glu-Glu-Leu-Gly-Ser-Asn-Thr-Gly-Ile-Gln-Val-Phe-Asn-Gln-Ile-Val-Lys-Ser-Arg-Pro-His-Asp-Asn-Ile-Val-Ile.

cDNA encoding the complete human PN-I protein was obtained from a foreskin fibroblast DNA library. The retrieval of this clone took advantage of probes based on the amino acid sequence determined in the native protein. The cloned cDNA is amenable to expression in recombinant cells of both procaryotic and eucaryotic organisms, as described above, by excising the coding sequence from the carrier vector and ligating it into suitable expression systems. The PN-I can be directly produced as a mature protein preceded by a Met N-terminal amino acid (which may or may not be processed, depending on the choice of expression systems) may be produced as a fusion protein to any desirable additional N-terminal or C-terminal sequence, or may be secreted as a mature protein when preceded by a signal sequence, either its own, or a heterologous sequence provided by, for example, the known signal sequence associated with the bacterial β-lactamase gene or with secreted human genes such as insulin or growth hormones. Means for providing suitable restriction sites at appropriate locations with respect to the desired coding sequence by site-directed mutagenesis are well understood, and the coding sequence can thus be provided with suitable sites for attachment to signal sequence or fusion sequence, or into expression vectors.

If bacterial hosts are chosen, it is likely that the protein will be produced in nonglycosylated form. If the PN-1 is produced intracellularly as a "mature" protein, the N-terminal methionine may be only partially processed, or not processed at all. Thus, the protein produced may include the N-terminal met. Modification of the protein produced either intracellularly or as secreted from such bacterial host can be done by providing the polysaccharide substances, by refolding using techniques to sever and reform disulfide bonds, or other post-translational ex vivo processing techniques. If the protein is produced in mammalian or other eucaryotic hosts, the cellular environment is such that post-translational processing can occur in vivo, and a glycosylated form of the protein is produced.

The recombinant cells are cultured under conditions suitable for the host in question, and the protein is recovered from the cellular lysate or from the medium, as determined by mode of expression. Purification of the protein can be achieved using methods similar to that disclosed by Scott, R. W., et al, *J Biol Chem* (supra), or by other means known in the art.

The purified protein is then formulated according to its application. For pharmaceutical application, the protein is formulated into compositions using standard excipients, as is understood by practitioners of the art, and disclosed, for example, in *Remington's Pharmaceutical Sciences*, latest edition, Mack Publishing Company, Easton, Pa. If to be used in diagnostic or immunoassay, the protein may be labeled using radioactive species, for example, or fluorescent markers. If it is to be used to obtain antibody preparations, the protein is prepared for injection along with suitable adjuvant. Methods of modifying the recombinant protein of the invention according to its desired use will be clear from the generally practiced techniques of the art.

Two forms of PN-I, PN-Iα and PN-Iβ are illustrated below. They are highly homologous and contain 378 and 379 amino acids, respectively in the mature sequence, differing only at position 310 where the Arg of PN-Iα is replaced by Thr-Gly in PN-Iβ. Both have a 19 amino acid signal beginning at Met. The location of the N-terminus is deduced form the sequenced native protein and it is highly likely this is correct; however, there is a small probability that alternate processing site(s) may also be utilized.

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

C.1. Hosts and Control Sequences

Both procaryotic and eucaryotic systems may be used to express the PN-I encoding sequences of the invention; procaryotic hosts are, of course, the most convenient for cloning procedures. Procaryotes most frequently are represented by various strains of *E. coli;* however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al. *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the β-lactamase (penicillinase) and lactose (lac) promoter systems (Chang. et al, *Nature* (1977) 198:1056) and the tryptophan (trp) promoter system (Goeddel, et al *Nucleic Acids Res* (1980) 8:4057) and the lambda-derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae,* Baker's yeast, are most used although a number of other strains or species are commonly available. Vectors employing, for example, the 2 μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L. et al, *Meth Enz* (1983) 101:300) may be used. Control sequences for yeast vectors include promoters for the synthesis of glycolytic enzymes (Hess, et al, *J Adv Enzyme Req* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular orgamisms. See, for example, Axel, et al, U.S. Pat. No. 4,399,316. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma. Adenovirus 2, bovine papilloma virus, or avian sarcoma viruses. The controllable promoter, hMTII (Karin, M., et al, *Nature* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA regions. Origins of replication may be obtained, if needed, from viral sources. However, integration into the chromosome is a common mechanism for DNA replication in eucaryotes.

C.2. Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the $RbCl_2$ method described in Maniatis, et al, *Molecular Cloning: A Laboratory Manual* (1982) Cold Spring Harbor Press, p. 254 and Hanahan, D., *J Mol Biol* (1983) 166:557-580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777-785 may be used. Transformations into yeast may be carried out according to the method of Beggs, J. D., *Nature* (1978) 275:104 ∩ or of Hinnen, A., et al, *Proc Natl Acad Sci (USA)* (1978) 75:1929.

C.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth in C.1 above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; Jay, Ernest, *J Biol Chem* (1984) 259:6311.

Synthetic oligonucleotides are prepared by either the phosphotriester method as described by Edge, et al., *Nature* (supra) and Dickworth, et al., *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing of for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles γ32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 µl volumes under the following standard conditions and temperatures: for example, 20 mM Tris-Cl ph 7.5, 10 mM MgCl$_2$, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per µg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487-6500 and Adelman, J. P., et al., *DNA* (1983) 2:183-193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

C.4. Verification of Construction

For confirmation of vector construction, or for other sequencing, DNA is first amplified and isolated. The isolated DNA is analyzed by restriction and/or sequenced by the dideoxy nucleotide method of Sanger, F., et al, *Proc Natl Acad Sci (USA)* (1977) 74:5463 as further described by Messing, et al., *Nucleic Acids Res* (1981) 9:309, or by the method of Maxam, et al., *Methods in Enzymology* (1980) 65:499.

EXAMPLES

The following examples are intended to illustrate but not to limit the invention. In one aspect, the examples detail a method to retrieve the desired cDNA sequences; however, this process need not be repeated. The complete DNA sequence for coding regions of the inserts in the PN-Iα and PN-Iβ clones are given in FIGS. 3 and 4, and standard synthetic methods may be used to construct either these precise sequences or the equivalent degenerate sequences employing alternate codons. Synthesis of DNA sequences of this length are by now nearly routine in the art. See, for example, Edge et al., *Nature* (1981) 292: 756. In addition, on Jun. 4, 1986, applicants have deposited at the American Type Culture Collection, Rockville, Md., the PN-18 clone in phage λgt10 having ATCC No. 40238. This contains the relevant coding sequence for PN-Iα, which can be manipulated starting from the physical substance; the PN-Iβ sequence can easily be obtained using site-specific mutagenesis.

EXAMPLE 1

Purification of Native Protease Nexin-I

PN-I was prepared from serum-free conditioned medium, as described in Scott, R. W., et al., *J Biol Chem* (1985) (supra). Briefly, the harvested medium was filtered through a 45 µ millipore filter, and the proteins concentrated by Amicon hollow fiber filtration. The concentrated medium from a single 3 1$^2$ microcarrier culture was passed over a 0.7×30 cm heparin-agarose column, preequilibrated in 0.3 M sodium chloride in phosphate buffer, and eluted with 1.0 M sodium chloride in phosphate buffer, both containing 0.02% sodium azide. Elution was obtained in 0.55-0.6 M NaCl. The PN-I-containing fractions were concentrated by dialysis and then subjected to gel-exclusion chromatography by dialyzing 1-2 mg PN-I in 1 ml into column buffer containing 0.5 M NaCl, and applied to a 1×60 cm Bio-Gel P-100 (Bio-Rad 100-200 mesh) column and eluted with column buffer. The peak fractions were concentrated to 1 ml and stored at −80° C. The amino acid sequence and sugar composition were determined on this purified material.

The N-terminal amino acid sequence for the first 34 amino acids was determined with the results set forth above.

EXAMPLE 2

Isolation of Protease Nexin-I cDNA

Human foreskin fibroblasts were grown to confluence in 30×150 mm flasks, as described by Scott, R. W., *J Biol Chem* (1983) 258:10439, yielding approximately $1-2\times10^8$ cells. Twenty-four hr prior to harvest, cells were refed to stimulate the production of PN-I mRNA. The cells were harvested in the cold and washed twice with phosphate buffered saline (PBS). The cell pellets were recovered, homogenized in buffer containing 20 mM vanadyl complex, and 0.2% Nonidet P-40 detergent, and then centrifuged for 10 min at 14,000 rpm. RNA was prepared from the supernatant using phenol/chloroform extraction and the total RNA obtained was subjected to oligo-dT affinity chromatography to obtain mRNA.

The isolated messenger was gel fractionated and probed with a mixture of twenty-four 14-mers having the sequence shown in FIG. 1a, which represents the degenerate reverse complement of DNA encoding amino acids 20-24 of the determined N-terminal sequence. The probe hybridizes to mRNA of approximately 2500-2700 nucleotides in length.

The total mRNA preparation was then used as a template to prepare a cDNA library in λgt10, substantially as described by Huynh, T. V., et al., *DNA Cloning Techniques: A Practical Approach* (1984), Glover, D., ed, IRL, Oxford, but with second-strand synthesis performed according to the method of Gubler, V., et al., *Gene* (1983) 25:263-269. the resulting cDNA was cut with EcoRI and inserted into the EcoRI site of λgt10, as described by Huynh et al. (supra). Several million phage plaques were obtained and triplicate filter lifts were prepared. Plaques were duplicate screened under conditions of moderate stringency (6×SSC at 30° C.), with the 5′ end $^{32}$P-ATP-labeled mixture of the 14-mers above. This resulted a number of positive clones.

Of the 60 clones picked and cultured, 48 of them also hybridized under comparably stringent conditions to a 36-nucleotide oligomer of the sequence shown in FIG. 1b, which was a consensus sequence designed on the basis of amino acids 14 ∝ 25, the sequence determined in the native protein.

Figure 2:
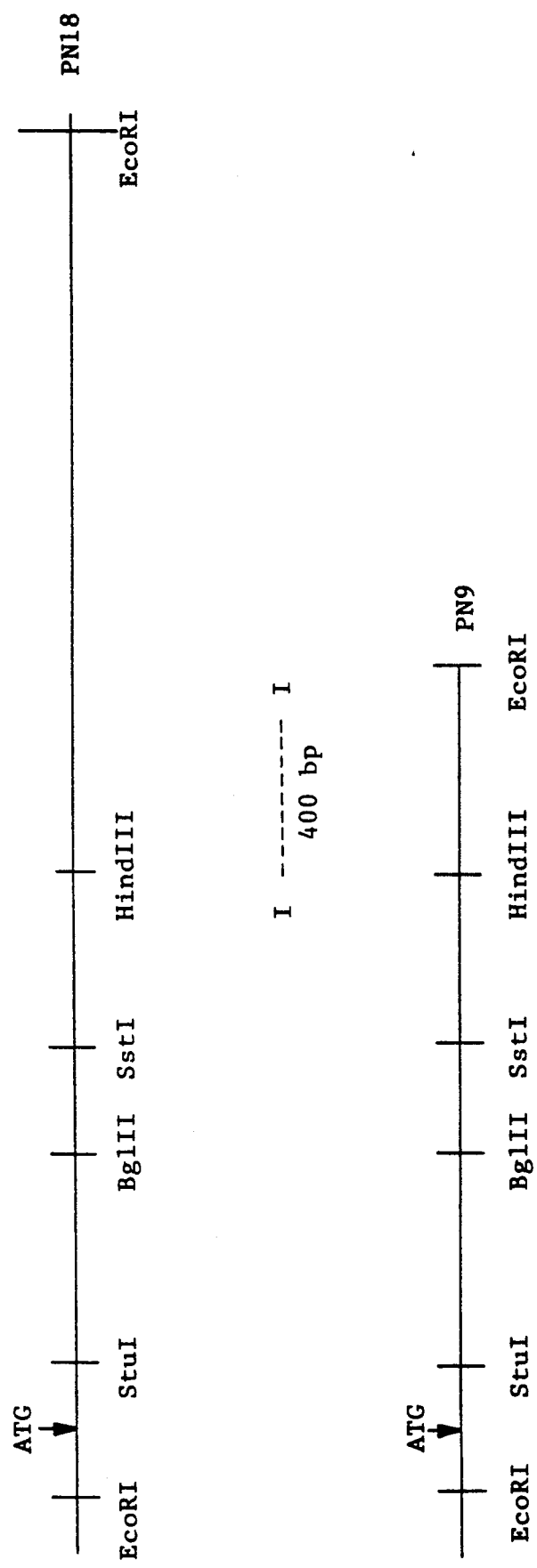
FIG. 2 shows restriction maps of the cDNA clones designated PN-9 (representative of the class to which PN-33 belongs) and PN-18, each of which contains the coding sequence for a complete PN-I protein. Restriction maps of the cDNA inserts PN-18 and PN-9. PN-18 is typical of the 3 kb inserts observed whereas PN-9 is representative of the 2 kb size class. The EcoRI sites at the 5' and 3' ends of the cDNA clones are derived from the EcoRI linkers used during the cloning procedure.

Fifteen of these 48 clones were of approximately the size expected from the mRNA to be of sufficient length to encode the entire sequence. These fell into two classes by size: 2000 bp and 3000 bp. One 3000 bp clone was designated PN-18, and one 2000 bp clone was designated PN-33. These clones have similar coding sequences. Clones, designated PN-5, PN-8 and PN-11 have the same coding sequence as PN-18; clone PN-9 has the slightly different coding sequence included in PN-33. Restriction maps show these clones to include the 5′ end of the gene; these maps are shown in FIG. 2.

PN-18 was restricted with Sau3AI and cloned into the BamHI site of M13. To confirm the presence of the correct cDNA, the resulting M13 subclones were screened with the 14-mer mixture. Also, a 55 bp fragment was sequenced and found to contain the correct sequence encoding amino acids 17-34 of the native protein.

Thirteen of the above 15 clones contained a 750 bp EcoRI-BglII fragment which hybridizes to the 14-mer probe and is believed to encode the 5′ portion of the gene. This segment has been sequenced, and the determined sequence includes the 55 bp Sau3AI fragment above, and the codons for the N-terminal sequence determined above, as well as codons for a putative 19 amino acid signal sequence extending back to an ATG.

The complete coding sequence for PN-Iα contained in PN-18 and the deduced amino acid sequence are shown in FIG. 3. The first 19 encoded amino acids are a putative signal sequence, and the first 34 amino acids of the putative mature protein starting at the serine at position 20 correspond exactly to the N-terminus of the native protein. PN-18 is deposited with the American Type Culture Collection, and has accession number ATCC 40238.

Figure 5:
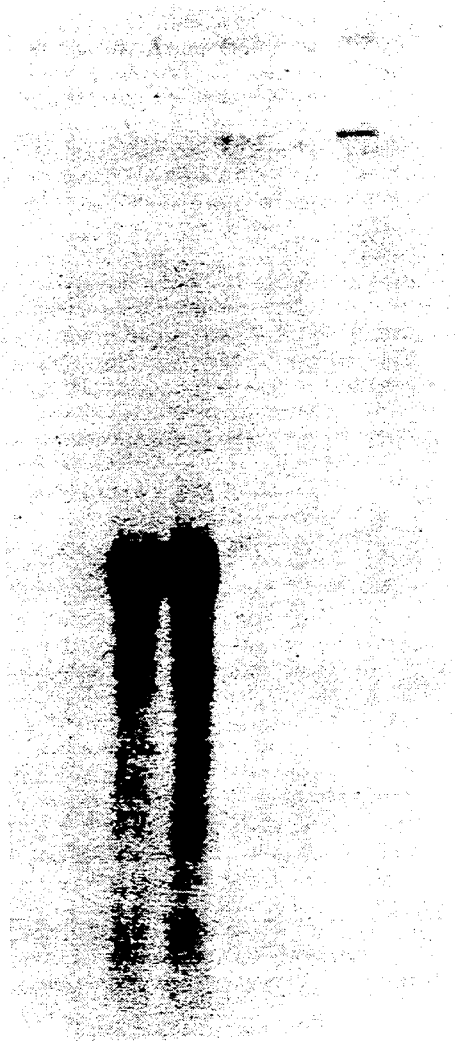
FIG. 5 shows a northern block of mRNA extracts from certain cell lines using a sau3AI fragments from PN-18 as a probe. The RNA samples were denatured and fractioned on a methyl mercury agarose gel which was electrophoretically transferred to a GENES-CREEN membrane filter. The pN-18 probe was prepared by primer extension of the M-13 clone in the presence of 32PdCTP. The RNA filter was hydridized in formamide hybridization buffer (50% formamide; 5xSSC, 2X DENHARDTS, 20 mM Sodium phosphate buffer pH7, 0.2% SDS, and 100 ug/ml yeast RNA) at 42° C. for 36 hours with $2 \times 10^7$ cpm of 32P labeled probe. The filter was washed 32P labeled probe. The filter was washed at 42° C. in 2XSSC containing 0.2% SDS and exposed to X-ray film.

Identification of PN-18 with PN-I production was verified by Northern blot, as shown in FIG. 5. The 55 bp Sau3AI fragment obtained from PN-18 was labeled and used to probe mRNA obtained from human foreskin fibroblasts and from several other cell lines not capable of PN-I production. The probe hybridizes only to the mRNA of about 2.8 kb from the PN-I-producing cells.

the PN-33 clone which contains the DNA encoding PN-Iβ was also completely sequenced in the coding region with the results shown, along with the deduced amino acid sequence, in FIG. 4. As with PN-Iα, the first 19 encoded amino acids are a putative signal sequence, and the first 34 amino acids of the mature protein starting at the serine at position 20 correspond exactly to the N-terminus of the native protein. The sequence encoding PN-Iβ is almost identical to that of PN-Iα, except for the inclusion of an additional codon for glycine after that at position 310 of the mature protein and substitution of a threonine for an arginine residue at that position. Thus, mature PN-Iα contains 378 amino acids; mature PN-Iβ contains 379.

The entire sequenced portions of PN-18 and PN-33 cDNA shown in FIGS. 3 and 4 are identical except for the codons corresponding to the above amino acid sequence change. This was verified to be a deference in mRNA splicing by using PN-18 as a cDNA probe to retrieve a portion of the PN-I gene from a human genomic library. Sequencing in the region of the amino acid difference, which occurs between 2 adjacent exons continuing into the introns separating them, established that there was a 3 bp difference in the splice site. These results are shown in FIG. 6. The A at the beginning of the codon at position 310 for arginine in PN-Iα is spliced 3 bp farther downstream into the next exon than is the corresponding A in codon 310 for PN-Iβ.

Probes designed spanning this coding region which includes the foregoing Arg of PN-Iα and the Thr-Gly of PN-Iβ were used to estimate the relative amounts of mRNA in human foreskin fibroblast preparations, and the relative amounts of cDNA in the corresponding cDNA libraries. The results of both of these Northern and Southern blots, respectively, showed that the two proteins are formed in approximately equal amounts. Thus, neither form appears to be "normal" or dominant.

The genomic DNA encoding the PN-I proteins was further studied as follows: Southern hybridization analysis of human DNA isolated from SK hepatoma cells was restricted with BglII, HindIII, or Eco RI. Duplicate sample sets were fractionated on an agarose gel and electroblotted to a membrane filter. The resulting blots were hybridized to $^{32}$P labeled probes; either the 2 kb PN insert (PN-33) or the 650 bp BglII fragment from the 5' end. Based upon the pattern of hybridization obtained with the complete PN-I probes, the PN gene was estimated to span at least 20 kb. As expected, the 5' probe hybridized to a subset of the PN-I specific fragments and only a single band was seen for each enzyme digest. These results are consistent with a single PN-I gene.

EXAMPLE 3

Murine PN-I cDNA

In a manner similar to that described in Example 2, a cDNA library prepared in λgt10 from mRNA extracted from mouse fibroblasts is screened with the 55 bp Sau-3AI fragment derived from PN-18. Phage hybridizing to this probe are then picked and cloned to obtain the desired murine PN-I cDNA.

EXAMPLE 4

Construction of Expression Vectors

The coding sequences from the EcoRI cassettes of PN-33 or PN-18 were each ligated into an amplifiable host expression vector pSTH-MDH described in copending application Ser. No. 07/010,871, filed Feb. 4, 1987, assigned to the same assignee and incorporated herein by reference and partially reproduced herein. The amplifiable DHFR sequences are under control of the native promoter and followed by the termination sequences of the hepatitis surface antigen gene. In the finished vector, the PN-I sequences are under control of the SV40 early promoter, and are also followed by hepatitis surface antigen termination sequences.

The DNAs encoding PN-Iα and PN-Iβ were inserted into the host vector pSTH-MDH, in place of the tPA expression cassette, using three-way ligations in which the 5' and 3' ends of the coding sequences and appropriate portions of the expression systems were inserted as separate fragments. For the construction of these vectors, pSNαH-dhfr and pSNβH-dhfr, substantially equivalent ligations were performed, but with the appropriate starting materials.

For construction of pSNαH-dhfr, pNexα-HBV3'RI, a vector containing the C-terminal-encoding portion of the gene followed by the hepatitis termination sequences was digested with BglII and EcoRI and the 3' end of the expression system isolated. The vector pSV-Nexα, which contains the 5' end of the expression system, was digested with BglII and SalI and the vector portion containing the nexin 5' end isolated. These fragments were ligated with the DHFR selectable marker, excised from pSTH-MDH by EcoRI/SalI digestion, in a three-way ligation and transformed into E. coli for selection and amplification. Plasmid DNA representing the desired construction, pSNαH-dhfr, was isolated from the successful transformants.

In a precisely similar manner, pSNβH-dhfr was constructed, but using pNexβ-HBV3'RI and pSV-Nexβ in place of the corresponding PN-Iα-containing vectors.

Common to these constructions is a vector containing the SV40 early promoter operably linked to the nexin 5' end which is common to both α and β forms. This intermediate vector, pSV-NexBalI, was constructed using PN-33, pUC18, and pSVoriHBV3'. PN-33 was cut with EcoRI to excise the PN-I-containing inserts, cut back with Bal31 and then digested with SacI to obtain a tailored nexin insert containing the 5' end through the ATG start codon. This fragment was ligated into a HincII/SacI-digested pUC18 vector fragment to obtain pUCNex-BalI. pUCNex-BalI was cut with HindIII and SalI to excise the nexin 5' end fragment common to the α and β forms which was then ligated into the HindIII/SalI-digested pSVori-HBV3' vector fragment (see below) to give the desired pSVNex-BalI.

An additional vector containing 3' sequences, pSVNex3'HBV, was constructed by digesting PN-33 with EcoRI and HpaI, isolating the 1650 bp fragment and ligating it into pUC18 digested with EcoRI and SmaI to obtain pUC-Nex3'. pUC-Nex3' was supplied with hepatitis termination sequences by digesting with HindIII and BamHI and ligating the isolated nexin 3' end into HindIII/BamHI-digested pSVori-HV3' (see below) to obtain the desired pSVNex3'HBV.

The two additional intermediate vectors, pSVNexα and pSVNexβ, were obtained using the 540 bp internal fragment from PN-33 or PN-18, as appropriate, and the corresponding 5' and 3' ends from pSVNex-BalI and pSVNex3'HBV. In each case, pSVNex-BalI was digested with BglII and SalI and pSVNex3'HBV with HindIII and SalI and ligated in the three-way ligation with the BglII/HindIII 540 bp internal fragment of PN-Iα from PN-18 or PN-Iβ from PN-33 to obtain pSVNexα and pSVNexβ, respectively. These were modified to place an EcoRI site at the extreme 3' end of the expression system by inserting the BglII/SacII insert of pSVNexα or pSVNexβ, as appropriate, into BamHI/SacII-digested pUC-HBV3'. The resulting vectors, pNexαHBV3'RI and pNexβHBV3'RI, were then used in the constructions described above. The resulting vectors, generically named pSNH-dhfr, are diagrammed in FIG. 7.

The vectors were transfected into COS-7 cells for transient expression, or into DHFR deficient CHO cells, which were then amplified in methotrexate and cultured for the production of PN-Iα or PN-Iβ. The PN-I is secreted into the medium as the signal sequence is retained in the construct and is compatible with the host cells.

The media of the transformed cells are assayed for PN-I production using the thrombin binding assay described by Eaton, D. L., et al, J Cell Physiol (1983) 117:175–185. Briefly, serum-free medium preincubated with confluent cell cultures for 72 hr was centrifuged to remove cell debris. Labeled thrombin ($^{125}$I-Th) at 0.1 μg/ml was incubated with this medium for 45 min at 37° C. $^{125}$I-Th-PN complexes were resolved by SDS-polyacrylamide gel electrophoresis using 7% gels, under conditions which do not dissociate the Th-PN complex, and quantitated in a gamma scintillation counter, assuming that PN and Th are present in equimolar amounts in Th-PN complexes. The complexes formed are confirmed to contain PN-I by immunoprecipitation with PN-I rabbit antiserum.

The results of this assay show the production of PN-Iα or PN-Iβ by appropriately transfected CHO or COS7 cells.

Appendix

Construction of pSTH-MDH pSVoriHBV3' contains the origin of replication and early and late promoters of SV40 upstream of the 3' termination sequences from the hepatitis B surface antigen gene with insertion sites for a foreign gene between them. pSVoriHBV3' is constructed from pML, SV40, and HBV. pML is digested with EcoRI, blunted with Klenow, and then digested with HindIII. The vector fragment containing the C. coli origin replication and the ampicillin resistance gene is isolated and ligated to the isolated 540 bp fragment containing the early and late promoters and origin of replication of SV40, obtained by digestion of SV40 DNA by HindIII and HincII. The resulting vector, designated pSVori, is then digested with BamHI for acceptance of a 585 bp fragment isolated from a BamHI/BglII digest of HBV DNA which contains the 3' termination sequences of the surface antigen gene. Correct orientation is confirmed by restriction analysis - digestion with HindIII and BamHI yields a 350 bp fragment from the correct vector. The resulting ligated vector, pSVoriHBV3', thus contains the SV40 promoter and origin sequences upstream of the HBV terminator and permits a coding sequence to be inserted conveniently between them.

Also prepared was ptPA-BAL17, which contains the tailored upstream portion of the tPA gene in a bacterial replication vector. The tPA cDNA is furnished by the vector pMON-1068, which is a bacterial vector containing an insert of the entire cDNA sequence obtained for tPA as described in Pennica, D. et al, *Nature* (1983) 301:214-221. Of course, any bacterial replication vector containing this coding sequence could just as well have been used, and the restriction sites designated below fall within the disclosed sequence of the tPA cDNA set forth in the *Nature* reference. pMON-1068 is first digested with BamHI to excise the tPA encoding cDNA and then with BAL-31 to chew back at each end of the gene. Digestion with BAL-31 was continued until analysis of the lengths and sequence of linear fragments indicated that the 5' end of the fragment was within 17 bp of the ATG start codon. The precise distance of chew-back is not critical so long as it is within sufficiently short distance to permit the ATG to be placed an operable distance from the promoter in the expression cassette. A separation in this fragment of the 5' terminus from the ATG of about 10 bp is, in fact, 7referred. The selected linear fragment was then digested with SacI, which cuts inside the coding sequence of the tPA gene, and the resulting blunt-SacI fragment was isolated. This contains the suitably tailored 5' end of the gene and was ligated into SacI/HincII-digested pUC13 to give the intermediate plasmid ptPA-BAL17.

pUC-DHFR was used as a cloning vector for the DHFR-encoding sequences, absent their associated control sequences. pUC-DHFR was constructed by digesting pDHFR-11 (Simonsen, C. C., et al, *Proc Natl Acad Sci USA* (1983) 80:2495-2499) with Fnu4HI, blunting with Klenow and then digesting with BglII to isolate the 660 bp fragment as there described, and ligating this fragment into pUC13 which had been digested with HincII and BamHI. Thus, pUC-DHFR represents a straightforward cloning vector for DHFR analogous to the ptPA-BAL17 vector described for the 5' portion of the tPA gene above.

Finally, a separate cloning vector for the termination sequences derived from the hepatitis B surface antigen gene, pUC-HBV3', was constructed by digesting HBV DNA with BamHI and BglII and isolating the 585 bp fragment, as described above, and ligating this fragment into BamHI-digested pUC13.

pSV-tPA17, which contains the full-length tPA coding sequence under control of SV40 promoter and HBV terminating sequences was prepared as a three-way ligation of the vector fragment from pSVoriHBV3' digested with HindIII and BamHI, which thus provides the promoter and terminator along with vector sequences; the 3' portion of tPA obtained by SacI/BglII digestion of pMON-1068; and the tailored 5' portion of the tPA coding sequence, which was obtained as a HindIII/SacI digest of ptPA-BAL17. The resulting ligation mixture was transfected into *E. coli*, the transformants selected for ampicillin resistance, and plasmid DNA containing the desired pSV-tPA17 isolated.

The counterpart vector for DHFR expression, designated pSV-DHFR, was also obtained in a three-way ligation. Again the vector fragment obtained from HindIII/BamHI digestion of pSVoriHBV3' was used to provide the control sequences, and the 5' and 3' portions of the DHFR coding sequence were obtained by digestion of pUC-DHFR with HindIII and SacI (partial) and with BglII and TaqI (partial), respectively. The ligation mixture was used to transform *E. coli*, ampicillin resistant transformants were selected, and plasmid DNA, designated pSV-DHFR was isolated.

A single plasmid containing a weak expression system for the DHFR coding sequence was also prepared. This plasmid, pMDH, was obtained in a 3-way ligation using the 1 kb fragment obtained by EcoRI/TaqI (partial) digestion of pDR34, the vector fragment from EcoRI/SalI-digested pML, and the 3' end of the gene isolated from SacI (partial)/SalI digested pSV-DHFR. (The pDR34 vector is described by Gasser, C. S., et al, *Proc Natl Acad Sci USA* (1982) 79:6522-6526, supra) and contains the mouse DHFR gene linked to its own promoter.) The resulting vector, pMDH, is analogous to pSV-DHFR, except that the DHFR gene is under control of the murine DHFR promoter. The weak expression cassette residing on pMDH and strong expression cassette residing on pSV-tPA17, when used in admixture to transfect suitable DHFR-deficient cells, thus constitute one embodiment of the expression system of the invention.

Finally, pSTH-MDH, which contains the expression cassettes for tPA and for DHFR on a single vector, was constructed as a three-way ligation of the appropriate isolated fragments of pSV-tPA17, pMDH, and pUC-HBV3'. pSV-tPA17 is digested with SacII and SalI, pMDH with EcoRI and SmaI, and pUC-HBV3' with SacII and EcoRI.

We claim:

1. An isolated DNA molecule which encodes mature protease nexin-I (PN-I) alpha of FIG. 3 or PN-I beta of FIG. 4 or encodes a PN-I protein encoded by a gene which is a naturally occurring allelic variant of the gene encoding PN-I alpha or PN-I beta.

2. The DNA molecule of claim 1 which further includes DNA encoding a signal sequence which is operably linked to said mature PN-1α or PN-1β.

3. The DNA molecule of claim 2 wherein the linked DNA encodes the signal sequence of mature human PN-I.

4. A probe which is capable of hybridizing to mammalian cDNA that encodes PN-I and which is selected from the group consisting of
   (1) the Sau3AI fragment of PN-18;
   (2) the 750 bp EcoRI-BglII fragment of PN-18;
   (3) the 14-mer of FIG. 1a; and
   (4) the 36-mer of FIG. 1b.

5. An expression vector comprising a DNA encoding a protease nexin I (PN-I) having the amino acid sequence of PN-I alpha of FIG. 3 or PN-I beta of FIG. 4, or having an amino acid sequence encoded by a gene which is a naturally occurring allelic variant of that encoding said PN-I alpha or PN-I beta
   wherein said expression vector is capable, when transformed into a host cell, of expressing said PN-I encoding DNA.

6. The expression vector of claim 5 wherein the PN-I encoding DNA includes DNA encoding an operably linked signal sequence.

7. A unicellular host cell transformed with the expression vector of claim 5.

8. The host cell of claim 7 wherein said host cell is a mammalian cell and wherein said vector comprises an SV40-derived promoter.

9. A method of producing PN-I alpha or PN-I beta which comprises culturing cells transformed with the expression system of claim 5 under conditions which induce the expression of said PN-I encoding DNA and recovering the PN-I protein produced.

* * * * *

UNITED STATES PATENT AND TRADEMARK OFFICE
CERTIFICATE OF CORRECTION

PATENT NO. : 5,278,049

DATED : January 11, 1994

INVENTOR(S) : Joffre B. Baker, et al

It is certified that error appears in the above-identified patent and that said Letters Patent is hereby corrected as shown below:

On title page, item [73] should read:

Assignees: Incyte Pharmaceuticals, Inc.
Redwood City, California

University of Kansas
Lawrence, Kansas

Signed and Sealed this

Twenty-ninth Day of August, 1995

Attest:

BRUCE LEHMAN

Attesting Officer

Commissioner of Patents and Trademarks